United States Patent
Rejai

[11] Patent Number: 6,024,716
[45] Date of Patent: *Feb. 15, 2000

[54] TAMPON APPLICATOR AND METHOD OF FORMING SAME

[75] Inventor: Jamshid Rejai, Dover, Del.

[73] Assignee: Playtex Products, Inc., Westport, Conn.

[*] Notice: This patent is subject to a terminal disclaimer.

[21] Appl. No.: 08/976,527

[22] Filed: Nov. 21, 1997

Related U.S. Application Data

[63] Continuation of application No. 08/747,713, Nov. 12, 1996, abandoned, application No. 08/342,777, Nov. 21, 1994, abandoned, application No. 08/173,142, Dec. 23, 1993, Pat. No. 5,389,067, which is a continuation of application No. 07/886,114, May 20, 1992, abandoned.

[51] Int. Cl.⁷ ...................................................... A61F 13/20
[52] U.S. Cl. ............................................... 604/14; 604/15
[58] Field of Search ............................... 604/11–18, 904; 229/DIG. 14; 493/269, 296, 408

[56] References Cited

U.S. PATENT DOCUMENTS

| | | |
|---|---|---|
| 3,204,635 | 9/1965 | Voss et al. . |
| 3,358,354 | 12/1967 | Voss et al. . |
| 3,433,225 | 3/1969 | Voss ......................................... 604/14 |
| 3,568,577 | 3/1971 | Voss et al. . |
| 3,572,339 | 3/1971 | Voss et al. . |
| 3,628,533 | 12/1971 | Loyer . |
| 3,683,759 | 8/1972 | Voss et al. . |
| 3,683,915 | 8/1972 | Voss . |
| 3,895,634 | 7/1975 | Berger . |
| 4,078,715 | 3/1978 | Larsson et al. . |
| 4,412,833 | 11/1983 | Wiegner . |
| 4,453,925 | 6/1984 | Decker ..................................... 604/14 |
| 4,479,791 | 10/1984 | Sprague . |
| 4,508,531 | 4/1985 | Whitehead . |
| 4,617,781 | 10/1986 | Ingersoll et al. . |
| 4,650,459 | 3/1987 | Sheldon . |
| 4,726,805 | 2/1988 | Sanders, III . |
| 4,755,164 | 7/1988 | Hinzmann . |
| 5,087,239 | 2/1992 | Beastall et al. . |
| 5,290,501 | 3/1994 | Klesius . |

FOREIGN PATENT DOCUMENTS 2 097 259  11/1982  United Kingdom .

OTHER PUBLICATIONS

Dr. White's "Contour" Rounded End Applicator Tampons Advertisement, Sep. 1984.

*Primary Examiner*—John G. Weiss
*Assistant Examiner*—Dennis Ruhl
*Attorney, Agent, or Firm*—Ohlandt, Greeley, Ruggiero & Perle, LLP

[57] ABSTRACT

A method for forming a tampon applicator having a dome shaped forward end is disclosed, in which the requisite ejection force for discharging the pledget from the applicator is reduced by bending the petals forming the domed tip about their base prior to final fabrication of the dome-shaped petal tip. Several orders of the sequential steps for bending the petals are disclosed. The resultant tampon applicator has weakened fibers at the base of its petal segments to provide a desired significant reduction of the pledget ejection force.

4 Claims, 4 Drawing Sheets

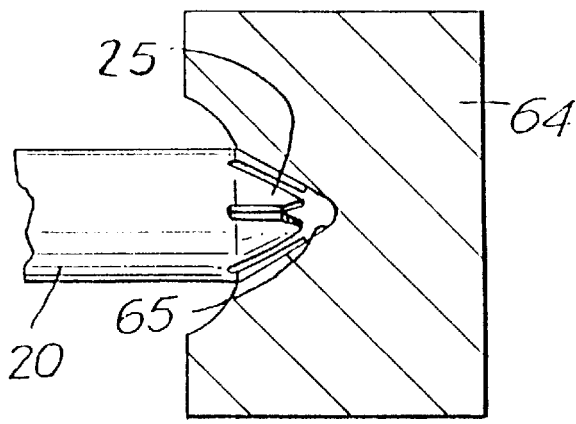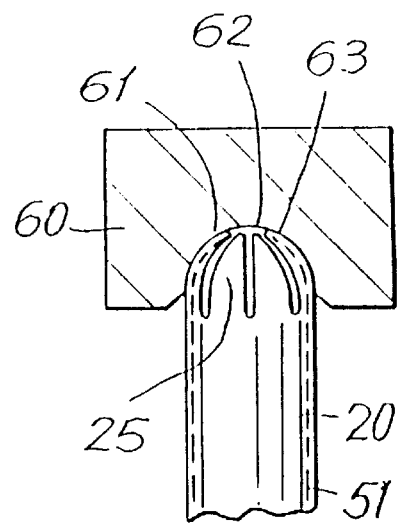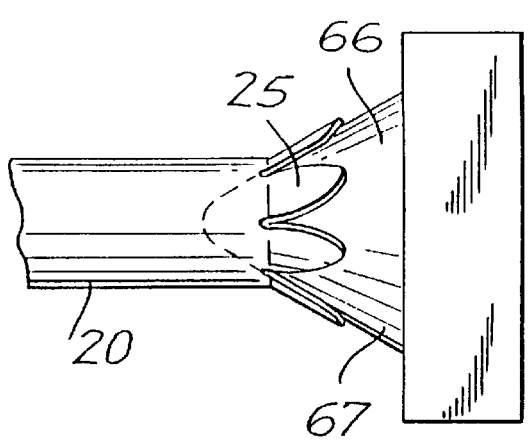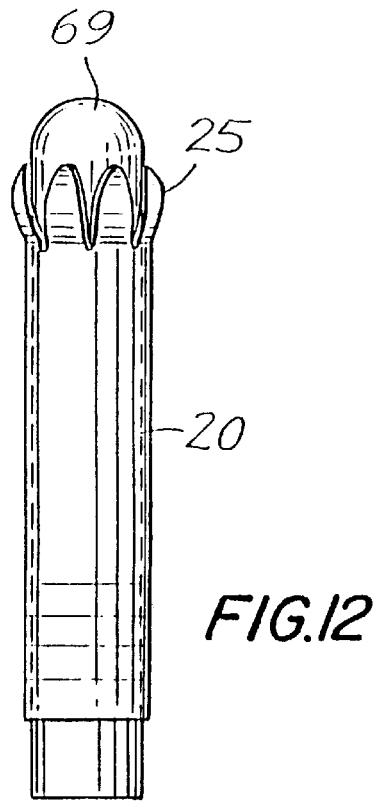
FIG. 9
FIG. 11
FIG. 10
FIG. 12

TAMPON APPLICATOR AND METHOD OF FORMING SAME

This application is continuation of application Ser. No. 08/747,713, filed Nov. 12, 1996 now abandoned, and a continuation of application Ser. No. 08/342,777, filed Nov. 21, 1994, now abandoned, and a continuation of application Ser. No. 08/173,142, now U.S. Pat. No. 5,389,067, which is a continuation of application Ser. No. 07/886,114, filed May 20, 1992 now abandoned.

This invention relates to telescoping-type applicators which have a dome shaped forward end and are intended for the storage and ejection of tampons, and to the method of producing such applicators to optimize the force required for the user to conveniently eject the tampon pledget from the applicator.

BACKGROUND OF THE INVENTION

Tampon applicators which include a pair of telescoping cylinders are well known in the art. For example, Berger, U.S. Pat. No. 3,895,634, assigned to the assignee of the subject application, and Voss U.S. Pat. No. 3,433,225 typically show such applicators in which the pledget is initially stored in the forward end of a cylindrical barrel. A lesser diameter plunger is telescopingly contained within the rear end of the barrel, such that the forward end of the plunger abuts the rear end of the pledget. Advantageously, the forward end of the barrel, which is inserted in the vagina prior to tampon injection, includes a smooth, dome-shaped end for the user comfort. When the user then urges the plunger against the rear end of the pledget, the pledget is moved forwardly in the barrel, opening up the petals which form the dome-shape forward end of the barrel, as the pledget is ejected from the barrel. Following the full ejection of the tampon pledget, the petals then return towards their original closed position so as to comfortably remove the applicator from the body orifice. Such tampon applicators are conventionally manufactured either of a suitable plastic composition, which is typically injection molded, or from cardboard. In view of environmental concerns, cardboard applicators, which are water degradable or water dispensable, are increasingly desirable. The force necessary to eject the tampon from a plastic applicator can be controlled by the composition and thickness of the plastic material, while maintaining the necessary structural integrity for the barrel. For example, in the aforementioned Berger U.S. Pat. No. 3,895,634 the cross-sectional wall thickness of the tubular portion of the barrel member and petals forming the dome-shaped insertion tip are different, to provide a relatively high strength side wall for the main body portion of the barrel and a relatively flexible and supple insertion tip. This provides the requisite stability for the barrel proper and an acceptable tampon ejection force. Achieving these desirable characteristics in a cardboard applicator is somewhat more difficult due to the limited degree to which the characteristics of the cardboard may be varied, as opposed to modifying the composition of the plastic, and the relative stiffness of cardboard layers which are of sufficient thickness to provide the requisite structural integrity for the barrel.

Various techniques have previously been proposed for modifying the forward end of such dome-shaped cardboard applicators which have petal defining slits to appropriately adjust the pledget ejection force. For example Wiegner, et al. U.S. Pat. No. 4,412,833 and Beastall et al. U.S. Pat. No. 4,087,239 provide an indented circumferential groove (which can take the form of slots or perforations in Beastall) at the end of the slits located at the base of the dome-shaped tip to provide a hinge region for the bending of the petals. Such a hinge had also been disclosed in aforementioned Voss et al. U.S. Pat. No. 3,433,225. Whitehead U.S. Pat. No. 4,508,531 and Decker U.S. Pat. No. 4,453,925 show a series of transverse score or relief lines along the length of the cardboard petals in a tampon applicator to facilitate their bending into a round tip.

While such prior techniques have been found to aid in the formation of the dome tip and lower or otherwise control the ejection force of the tampon pledget, they are less than fully satisfactory in appropriately optimizing the ejection force, while maintaining all the other desirable tampon applicator characteristics. Further, recognizing that some variations are to be expected in the mass production of tampon applicators it is desirable to provide for anticipated manufacturing tolerances to assure that appropriate ejection forces will still be maintained within the anticipated range of product variations.

SUMMARY OF THE INVENTION

In accordance with the present invention, during the manufacture of the barrel, the petals forming the dome tip are reverse bent at their base region in a direction other than that required to thereafter form the dome tip. It has been determined that this will provide a significant reduction in the ejection force for their subsequent opening, while maintaining the structural rigidity of the tampon barrel, petal tip stability and the other requisite applicator characteristics.

According to a preferred method employed for fabricating the tampon applicator in accordance with my invention, the cylindrical tube is first formed with the petals in alignment with the longitudinal axis of the cylindrical tube such that the forward end of the cylindrical tube is completely open. The petals are then bent radially inward towards the longitudinal axis of the cylinder, typically approximately 30 degrees. The petals are then bent radially outward in the opposite direction outside of the cylindrical volume defined by the cylindrical tube and beyond their original disposition, approximately an additional 30 degrees. The petals are then again moved inwardly towards the longitudinal axis, beyond the initial bending, and shaped to form the curved dome tip. During this reverse bending, there will be weakening of the cardboard at the base region of the petals. It is believed that such weakening occurs from the breaking of the fiber bonds between cardboard fibers at the petal base region. It has been observed that in a typical applicator fabricated according to this method, wherein the petals are first bent inwardly and then outwardly prior to the forming of the dome tip, the reduction of ejection force may be in the order of 25 percent.

My method may be employed both in conjunction with, or without, a circumferential hinge groove at the base region of the petal. Where the groove is provided, the reduction in ejection force contributed by the groove is additive to that achieved by the petal bending of the instant invention, so as to further reduce the ejection force towards the desired magnitude.

My invention may also be practiced in conjunction with that disclosed in Klesius, U.S. application Ser. No. 07/886,119, filed on May 20, 1992, and assigned to the assignee of the instant application, which is herein incorporated by reference, in which the petals are sprayed with a desired amount of moisture prior to final forming of their dome-shaped tip in order to provide increased petal stability during applicator storage.

In accordance with an alternative method for practicing the instant invention, after the cylindrical tube is formed with the individual petals extending forwardly so that the tube is completely open, the petals are then curved inwardly to form the dome-shaped end. Thereafter, the petals are moved radially outward of the volume defined by the cylindrical tube such that they make an angle of approximately 30 degrees from their original disposition. The petals are then moved inwardly to again form the dome-shaped tip. While this alternative technique requires a more extensive initial step, and thereby may be somewhat more expensive to practice, it too will provide fiber weakening and hence a reduction in tampon ejection force.

Still another alternate method, which involves less steps and, correspondingly may provide a lesser magnitude of cardboard weakening and reduction in ejection force may be practiced. This alternative technique involves first bending the petals outward from their original position, parallel to the longitudinal axis of the barrel, and then bending the petals in the reverse direction inwardly to form the dome-shaped tip.

A common theme present in all the methods for practicing my invention is the bending of the petals at their base region prior to the final formation of the dome tip. This sufficiently weakens the petals at their base region to obtain the requisite reduction in tampon pledget ejection force. Such weakening is achieved in conjunction with the other parameters of a particular cardboard applicator size so that the applicator possesses all the requisite parameters for acceptable performance.

It is accordingly a principal object of my invention to provide a method for forming a tampon applicator tube having a dome-shaped forward end, in which the required force for ejecting the tampon pledget is controllingly reduced a desired amount.

A further object is to provide such a method for forming a tampon applicator tube in which the petals are reverse bent about their base region prior to final fabrication of the dome-shaped tip.

Another object of my invention is to provide a cardboard tampon applicator having a dome-shaped tip in which the cardboard fibers at the base region of the petals forming the dome-shape are weakened at their base region by prior inward and outward radial movement of the petals with such fiber weakening providing a significant reduction of the ejection force subsequently required to open the petals forming the dome-shaped closure and expel the pledget from the forward end of the barrel.

These as well as other objects of my invention will now be further described and illustrated by reference to the accompanying drawings in which:

BRIEF DESCRIPTION OF DRAWINGS

FIG. 9 shows the production tool which may typically be used to thereafter transform the petals from the condition shown in FIG. 5 to that shown in FIG. 6A.

FIG. 10 shows the production tool which may typically be used to transform the petals from the condition shown in FIG. 6A to that in 6B.

FIG. 11 shows the production tooling for forming the petals into the dome-shaped tip.

FIG. 12 refers to the second embodiment, and particularly how the petals 25 of the initially formed dome-shaped tip are then outwardly bent.

DESCRIPTION OF THE PREFERRED EMBODIMENTS

Figure 1:
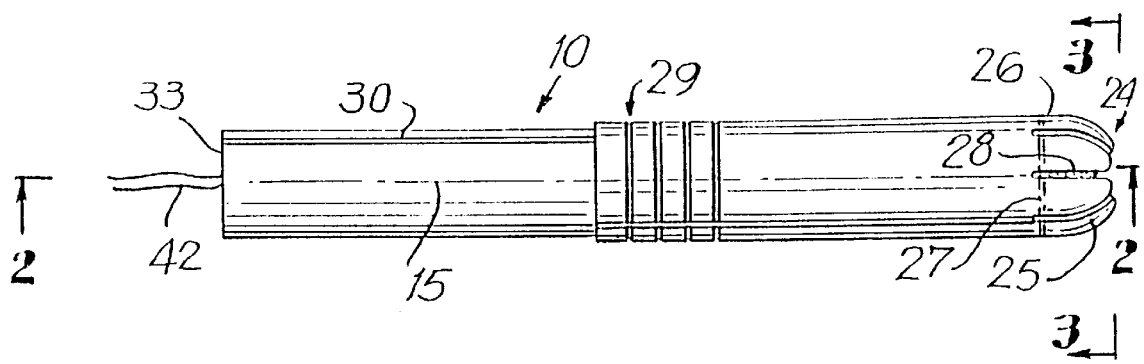
FIG. 1 is a side view of an assembled tampon applicator, including the pledget contained therein, constructed in accordance with my invention.
Figure 2:
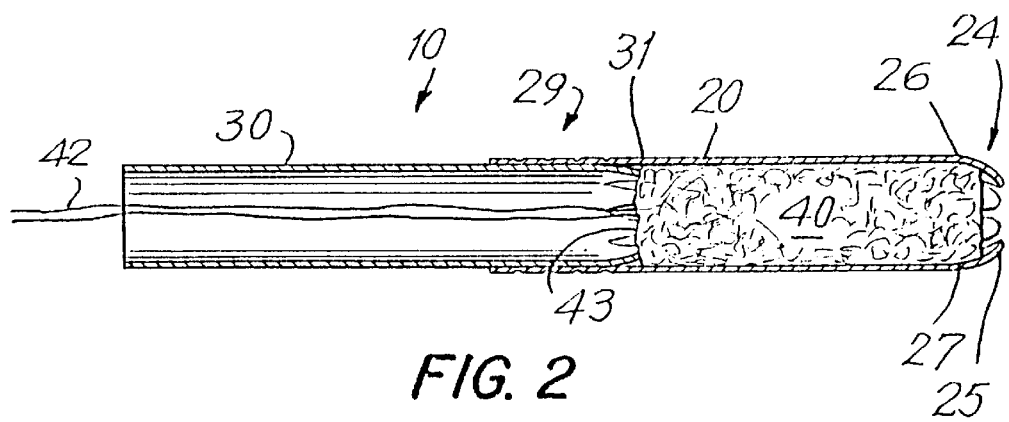
FIG. 2 is a cross-sectional view of the tampon applicator assembly shown in FIG. 1.
Figure 3:
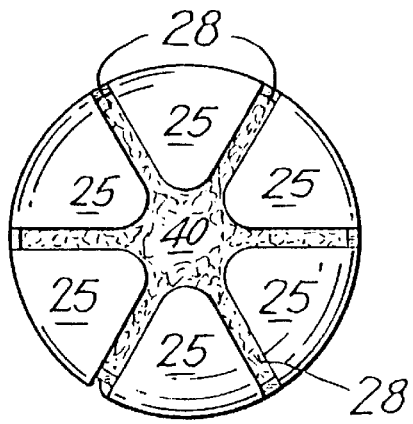
FIG. 3 is an end view of the tampon applicator assembly, in the direction of arrows 3—3 as shown in FIG. 1.

Referring initially to FIGS. 1–3, the tampon assembly 10 includes a cylindrical tube which forms a barrel 20. A plunger 30 is telescopingly contained within the rear end portion of the barrel 20. A tampon pledget 40, which may partake of various known prior art pledget constructions, such as for example that shown in aforementioned Berger U.S. Pat. No. 3,895,634, is initially positioned within the main cylindrical body of the assembled barrel member 20. A withdrawal string 42 extends outwardly through the central portion of the plunger 30 for subsequent removal of the pledget from the user's body after ejection from the applicator assembly, and removal of the applicator from the user's body. The forward end 31 of the plunger typically abuts the rear end 43 of the pledget for moving the pledget forward, in the conventional manner so as to eject the pledget 40 from the forward end of the barrel.

the barrel 20 includes a dome shaped forward end 24 which is provided for more comfortable insertion of the applicator. The dome end is typically shown as comprising six individual petals 25 which are curved inwardly at their base region. Although six petals are shown a different number of petals may be employed, as is well known in the art. To aid in such inward folding a circumferential groove, shown as 27 is preferably provided around the inward surface at the petal base region. The groove 27, which is preferably embossed on the blank 50 (see FIG. 4), while it is in the flat state may preferably be formed by a pair of complementary members (not shown), which contact opposite surfaces of the blank. One such member includes a circumferential projection corresponding to the groove to be formed at the base region. The other has a complementary circumferential recess. The coaction of the two members crush the fibers at the petal base region, thereby providing a hinge point to facilitate inward bending of the petals to their required dome configuration. Alternatively, the groove may be formed on the outside of the cylindrical barrel, or the groove may be omitted, with the requisite reduction in expulsion force being obtained by the appropriate characteristics of the cardboard, in conjunction with the initial bending of the petals at their base region 26 in accordance with my invention.

Figure 4:
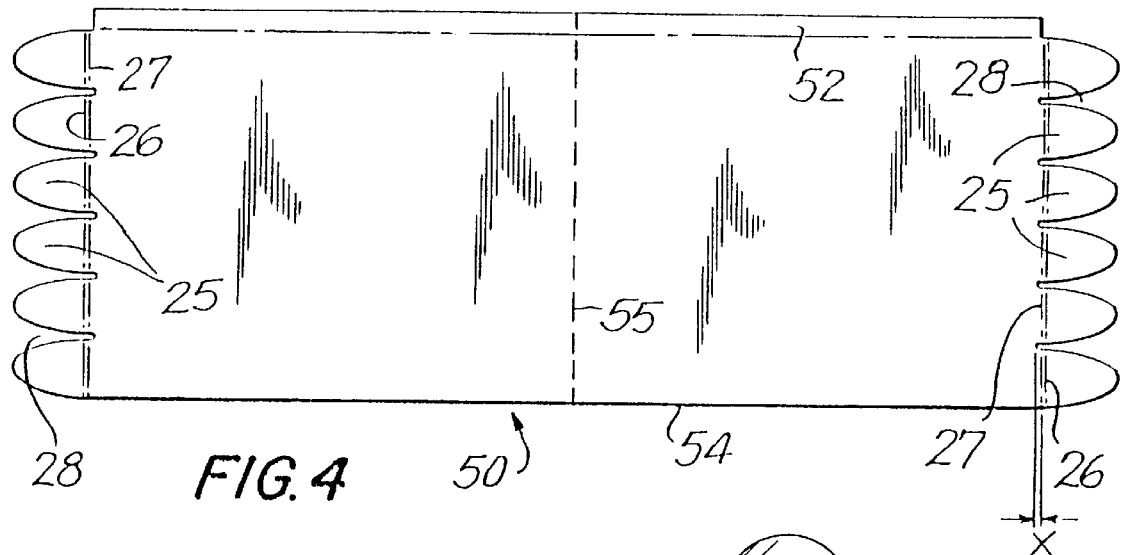
FIG. 4 shows a cardboard blank which may be used to form a pair of convolutely wound applicator barrels which are thereafter treated in accordance with my invention.

It is preferable for the radial slits 28 between the sides of the petals to extend somewhat below the base region 26 of the petals, and the circumferential groove 27 at the base region. Advantageously, this allows for tolerances with respect to anticipated manufacturing variations in the location of the groove. The circumferential groove 27 is not below the terminus of the radial slit 28. This displacement X, as shown in FIG. 4 (and as also shown in FIG. 4 of the aforementioned Ser. No. 07/886,119, between the groove 27 and lower terminus of slit 28, provides a region to facilitate the radially bending of the petals 25.

A finger grip section 29 is advantageously provided at the rear end of the barrel so as to facilitate the user's grasping and maintaining the applicator during pledget ejection, particularly if the outer surface of the applicator is made smooth, to aid in comfortable applicator insertion. As is well known in the art, the fingergrip may be formed by a plurality of score lines, such as for example, typically shown in aforementioned Wiegner et al. U.S. Pat. No. 4,412,833, or Jaycox U.S. Pat. No. 3,696,812. Although eight score lines are shown in FIG. 1, other numbers may be used, depending upon such factors as the thickness and smoothness of the cardboard forming the barrel 20.

Reference is now made to FIG. 4 which shows a blank 50 used to fabricate a preferred form of the barrel 20 in accordance with my invention. A pair of barrels 20 will be convolutely wound from blank 50. However spiral wound barrels may also be employed in conjunction with my invention. For economical purposes, it is advantageous to first form the blank 50 of a length to fabricate two barrels 20. That is, the blank 50 which is naturally twice the length of a single barrel, includes the petals 25 at each of its ends. In a preferred embodiment fabricated in accordance with our invention, the blank 50 forming the barrel, as well as the plunger 30, are made of a laminated paper/paper board stock. The radially inward laminates provide the requisite form and rigidity. The outermost layer is selected to provide appropriate smoothness and whiteness. Typically the inner plies may additively be in the order of 0.0135 to 0.0180 inches thick, with the outer ply being a wax coated paper stock in the order of 0.0018 inches thick. As is well known in the art, a thicker ply would typically be used for larger diameter size tampon pledgets, which likewise include a somewhat greater diameter barrel. The circumferential groove 27 is preferably embossed on the blank while it is in the flat state. Groove 27, is typically 0.02 inches wide, and 0.004–0.010 inches deep. This circumferential groove 27 may typically be 0.020–0.030 inches above the terminus of radial slit 28 as shown by the distance X in FIG. 4.

To form the barrel, the blank 50 is rolled into a cylinder and the opposite ends 52–54 which overlap are glued together. The unit is then cut along mid-section 55 to provide two identical barrels 20 in which the petals 25 extend forwardly in alignment with the longitudinal axis 15 of the barrel. In accordance with the typical prior art barrel formation, the forward end 24 of the barrel 20 would then only be presented against the petal forming tool 60 as shown in FIG. 11 which includes an inwardly concave surface 62 corresponding to the dome-shaped tip. In some situations, the tool 60 may be heated, typically to about 350 degrees Fahrenheit. This is particularly desirable if the outer coating of the barrel includes a thermo-sensitive material, as is disclosed in Whitehead, U.S. Pat. No. 4,508,531, to aid in forming the tip. During tip formation an inner mandrel 51, which may not be independently heated, is inserted within the barrel 20. Mandrel 51 has a forward curved end which is complementary to the concavity 63 of the heated forming tool 60.

Figure 5:
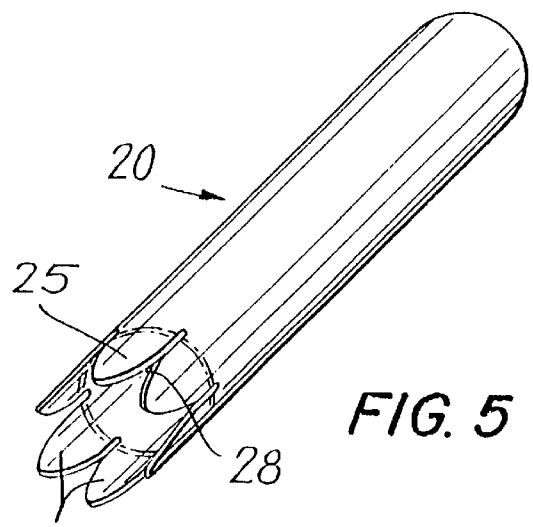
FIG. 5 shows one of the barrels formed from the blank of FIG. 4, with the petals in the fully open condition, prior to forming the dome-shape, as shown in FIGS. 1–3.

In accordance with my invention, additional intermediary steps are provided between the fabrication of the barrel from its condition shown in FIG. 5 to its dome-shape as shown in FIGS. 1–3.

Figure 6A:
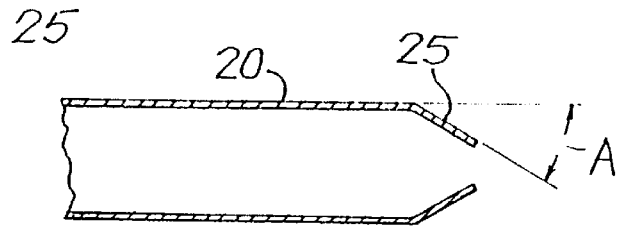
FIGS. 6A–6C show a preferred method of practicing my invention for sequentially forming the dome-shaped tip of the applicator from the initial condition shown in FIG. 5.
Figure 6B:
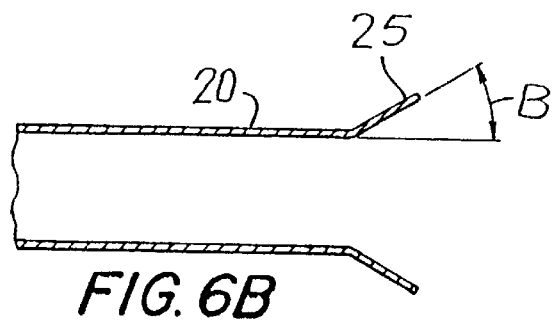

In accordance with one preferred method of practicing my invention, the petal tips sequentially go through the steps shown in FIGS. 5, 6A, 6B and 6C. The cylindrical barrel with open petals 25 as shown in FIG. 5 is first presented to the forming tool 64 as shown in FIG. 9. Forming tool 64 includes an inner concave surface 65 into which the petals 25 are only partially inserted so they are bent inwardly, but not closed, to the condition shown in FIG. 6A. Typically the inward bending petals, as shown by angle A, may be in the order of 30 degrees. The forward end of the barrel 20 is then presented to forming tool 66 as shown in FIG. 10. Forming tool 66 includes an outwardly cone shape forming surface 67 which is inserted within the open end of the barrel so as to outwardly deflect the petals 25 outside of the cylindrical column defined by the cylindrical tube or barrel 20, as shown in FIG. 6B. Typically, the angle B, through which the petals are reversed in the opposite direction may also be in the order of 30 degrees. Naturally, other magnitudes of inward and outward deflection of the petals 25 may be practiced, according to the characteristics of the cardboard forming the barrel 20, whether the circumferential hinge 27 is included, the dimensions of the barrel and petals and the desired final ejection pressure.

The forward end of the barrel is then formed into the final dome-shape as by tools 51 and 60 generally corresponding to that shown in FIG. 11. Tool 60 includes inward concave surfaces 61, which are preferably heated (typically in the order of 350 degrees Fahrenheit), which curves the individual petals 25 to partake of the configuration shown in 6C which, corresponds to the dome-shaped forward end of the barrel 20 in the completed assembly 10, shown in FIGS. 1–3. The pledget 40 and plunger 30 are then inserted through the rear of the barrel 20 to provide the complete operative assembly. The assembly 10 is then typically wrapped in an individually sealed package, as for example shown in Ingersoll, et al. U.S. Pat. No. 4,617,781, assigned to the assignee of the instant application.

Thus, it will be seen in referring to the sequential steps of FIGS. 5, 6A, 6B and 6C, that there is a radially inward and outward bending of the individual petals 25 about their base region 26 prior to the final fabrication of the dome shaped tip. It has been determined, as will be discussed below, that such bending of the petals will provide a significant reduction in the force required to thereafter eject the tampon pledget 40 through the dome shaped forward end 24 of the applicator barrel 20. It is believed that this reduction results from the breaking of bonds between the individual cardboard fibers at the base region 26 of the petals 25. This breaking of the fiber bonds weakens the fibers, with the effect of such weakening being generally additive to the weakening of the fibers achieved by their crushing to form the circumferential hinge groove 27.

Figure 6C:
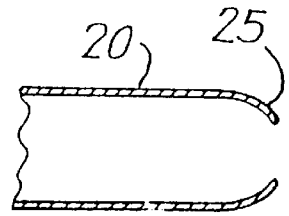

Reference is now made to another sequential method for practicing my invention, which sequentially follows the steps shown in FIGS. 5, 6C, 12 and 11. The open forward end 24 of the open barrel 20, as shown in FIG. 5 is first formed to the dome tip as shown in FIG. 6C such as by tools 51 and 60 shown in FIG. 11. The petals 25 are then opened outwardly to the condition shown in FIG. 12. This may be performed as shown in FIG. 12 by a spherical shape mandrel 69 which is inserted within the barrel 20 from the rear end so as to move the petals 25 outwardly. The manual 69 is then removed and the petals reverse formed inwardly to the conditions shown in FIG. 11. As was the situation with respect to the method discussed in conjunction with FIGS. 6A–6C, this alternative method likewise radially bends the petals 25 in both directions about their base region prior to final tip fabrication, with this embodiment including the step of first preforming the petals into the dome-shape. This alternative embodiment also provides for petal weakening, and hence a reduction in ejection force.

Figure 7A:
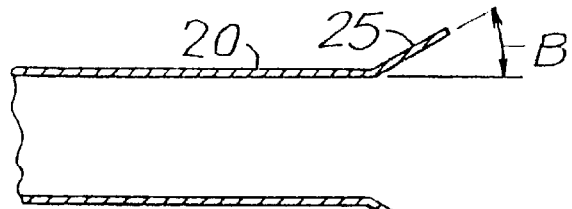
FIGS. 7A–7C show some of the steps of an alternative method for sequentially forming the dome-shaped applicator from the initial condition shown in FIG. 5.
Figure 7B:
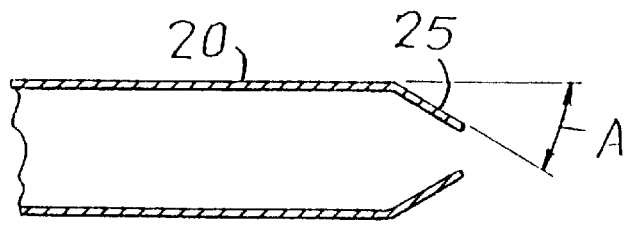
Figure 7C:
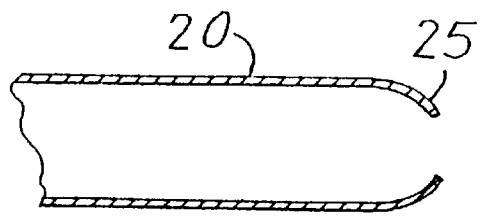
Figure 8A:
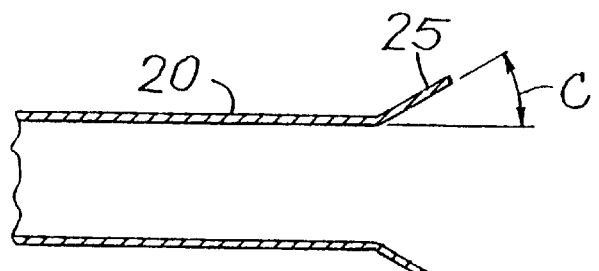
FIGS. 8A and 8B sequentially shows some of the steps of a third embodiment of the method for forming the dome-shaped applicator from the cylindrical barrel shown in FIG. 6.
Figure 8B:
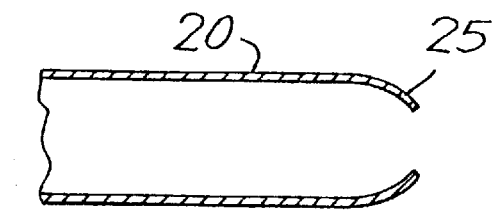

Still a further, and simpler method is shown in the alternative embodiment, of FIGS. 8A and 8B. According to this embodiment the petals of the barrel are modified from the condition shown in FIG. 5 to an outward bending as shown in FIG. 8A, (which generally corresponds to FIGS. 7A and 6B). This outward bending may be accomplished by a tool such as 66 shown in FIG. 10. The petals are then moved inwardly to form the dome-shaped configuration shown in FIG. 8B, such as by tools 51 and 60 of FIG. 11. If desired, an intermediate step may be included of first bending the petals inwardly, such as generally corresponding to the condition of FIGS. 6A or 7C, before their final shaping to the dome configuration. Further, by suitbly varying the conical shape of tool 66 the angle C of outward deflection as shown in FIG. 8A may be increased, from the 30 degrees shown by angle B in FIG. 6B, due to the lesser number of steps, in order to achieve the requisite degree of petal weakening and reduction in ejection force.

The particular method selected, and extent of petal deflection prior to forming, naturally depends upon the characteristics of the particular cardboard stock selected for forming the barrel, the measured ejection force without incorporating the steps of my invention, whether or not a circumferential groove is provided at the base region of the petals, and the desired degree of ejection reduction.

I have measured the reduction in ejection force achieved by the preferred method of FIGS. 6A–6C, both with and without the circumferential groove 27. Each test comprised 20 barrels. In order to account for aging after initial manufacture, four tampon assemblies 10 from each test cell were tested at the time of initial manufacture, and on each of four successive days. The ejection force measured in ounces, was measured on a top loading spring balance. The measurement was achieved by an individual grasping the fully assembled tampon assembly 10 of FIG. 1, in its intended manner, with the thumb and index finger being along the ginger grip 29. The assembly was held in a vertical position with the outwardly extending plunger end 33 placed on top of the balance. A slow downward motion was then applied to the barrel until the tampon pledget 40 was ejected from the barrel 20 by the resistance of the scale balance. The maximum scale reading was then recorded as the pledget ejection force.

With the circumferential groove 27 the measured average ejection force without the practice of my invention was 18.4 ounces, whereas the average ejection force measured in with the practice of my invention was 12.2 ounces. Hence, a reduction of ejection force of 6.2 ounces, or slightly above 33 percent was obtained according to the preferred method of this invention.

The same test was also run with barrels 20 which did not include the groove 27 to provide a petal hinge. A comparable reduction in ejection force was achieved with the practice of my invention. The measured ejection force without my invention averaged 21.0 ounces, and with my invention 15.1 ounces. Hence a differential of 5.9 ounces, or approximately 28 percent was obtained. It should be further noted that a reduction of ejection force achieved by the petal bending method of the instant invention is generally in addition to that achieved by the groove 27 at the base region of the petals 25.

Since a sufficiently low ejection force to conveniently discharge the pledget from the applicator is a very desirable consumer requirement, my invention advantageously provides an effective method for achieving the requisite ejection force. Further, it should be appreciated that by varying the steps, as shown by the different methods disclosed, as well as the degree of petal bending, the reduction of ejection force can be adjusted according to the characteristics of the cardboard forming the applicator and size of the barrel 20 and petals 25.

Other modifications of the present invention will be obvious to those skilled in the art in the foregoing teachings. Moreover, while the present invention has been described with reference to specific embodiments and particular details thereof, it is not intended that these details be construed as limiting the scope of the invention, which is defined by the following claims.

I claim:
1. A tampon applicator comprising:
   a cylindrical cardboard barrel having a main cylindrical body with a longitudinal central axis and a rear end, and having a dome-shaped forward end opposite the rear end, the barrel having individual cardboard fibers;
   an ejector tube having a first end that is adapted to be slidably retained by the rear end of the main cylindrical body,
   the main body having a circumferential groove adjacent the dome-shaped forward end, wherein the dome-shaped forward end and a portion of the main cylindrical body have a plurality of individual petals separated by a plurality of slits that extend from the dome-shaped forward end, past the groove to a terminus of slits,
   wherein the individual petals have a base region at the groove, and wherein the individual petals have been bent back and forth to break bonds, creating a weakened area at the base region, prior to formation of the dome-shaped forward end.
2. The tampon applicator of claim 1, wherein said cylindrical cardboard barrel is convolutely wound.
3. The tampon applicator of claim 1, wherein said base region has cardboard fibers in which the fiber bonds therebetween are broken prior to formation of the dome-shaped forward end, and wherein the broken bonds weaken the cardboard fibers to provide a reduction of the ejection force required to eject a pledget from the dome-shaped forward end.
4. A tampon applicator comprising:
   a first member capable of housing an absorbent tampon, said first member having an inside diameter, and a first and a second spaced apart end;
   an insertion tip formed adjacent to and at least partially closing said first end, said insertion tip having a plurality of individual petals separated by a plurality of slits, each individual petal having a base region, wherein the individual petals are bent back and forth to break bonds between individual cardboard fibers at the base region, and
   an ejector tube having a first end that is adapted to be slidably retained by said second spaced apart end of said first member.

\* \* \* \* \*